United States Patent [19]
Sato et al.

[11] Patent Number: 5,206,170
[45] Date of Patent: Apr. 27, 1993

[54] SULFUR DIOXIDE DETECTOR DEVICE EMBODIED BY USING SO2-OXIDANT BIOAGENT

[75] Inventors: Takeshi Sato, Toki; Nobuko Kubo, Anjyo; Hirofumi Akano, Handa; Yoshiya Kawamura, Kounan; Shigesada Iijima, Nukata, all of Japan

[73] Assignee: Nakano Vinegar Co., Ltd., Handa, Japan

[21] Appl. No.: 769,534

[22] Filed: Oct. 1, 1991

[30] Foreign Application Priority Data

Mar. 28, 1991 [JP] Japan .................................. 3-64951
Mar. 28, 1991 [JP] Japan .................................. 3-65004

[51] Int. Cl.$^5$ ................... G01N 27/327; C12M 1/34
[52] U.S. Cl. .................................... 435/211; 204/403; 435/289; 435/817
[58] Field of Search ............... 435/817, 291, 288; 204/415, 403, 153.17, 153.19

[56] References Cited

U.S. PATENT DOCUMENTS

| | | | |
|---|---|---|---|
| 3,715,298 | 2/1973 | Goodson et al. | 435/291 X |
| 4,017,374 | 4/1977 | Aas et asl. | 204/195 P |
| 4,235,687 | 11/1980 | Romette et al. | 204/195 M |
| 4,297,173 | 10/1981 | Hikuma et al. | 204/1 T |
| 4,374,013 | 2/1983 | Enfors | 435/817 X |
| 4,667,504 | 5/1987 | Hobson | 73/38 |

FOREIGN PATENT DOCUMENTS

5660342 5/1981 Japan .................................. 435/817

Primary Examiner—Peter Kratz
Attorney, Agent, or Firm—Cooper & Dunham

[57] ABSTRACT

In a sulfur dioxide detector using SO$_2$-oxidant microbes, a bio-membrane is located at one end of an oxygen concentration sensor, the bio-membrane containing the SO$_2$-oxidant microbes between an immobilized membrane and a gas permeable membrane. The sensor has an electrode in contact with the immobilized membrane. A dish-shaped or frusto-conical cell has an open end which is in contact with the gas permeable membrane so that SO$_2$-laden solution supplied to the cell causes sulfurous acid to oxidize to sulfuric acid as the SO$_2$ permeates through the bio-membrane so as to change an output from the sensor. An inlet and outlet hole are formed on a sidewall of the cell. The outlet hole is located to be always directly above the inlet hole so as to drain foam formed when the SO$_2$-laden solution is supplied to the cell through the inlet hole and drained from the outlet hole.

7 Claims, 3 Drawing Sheets

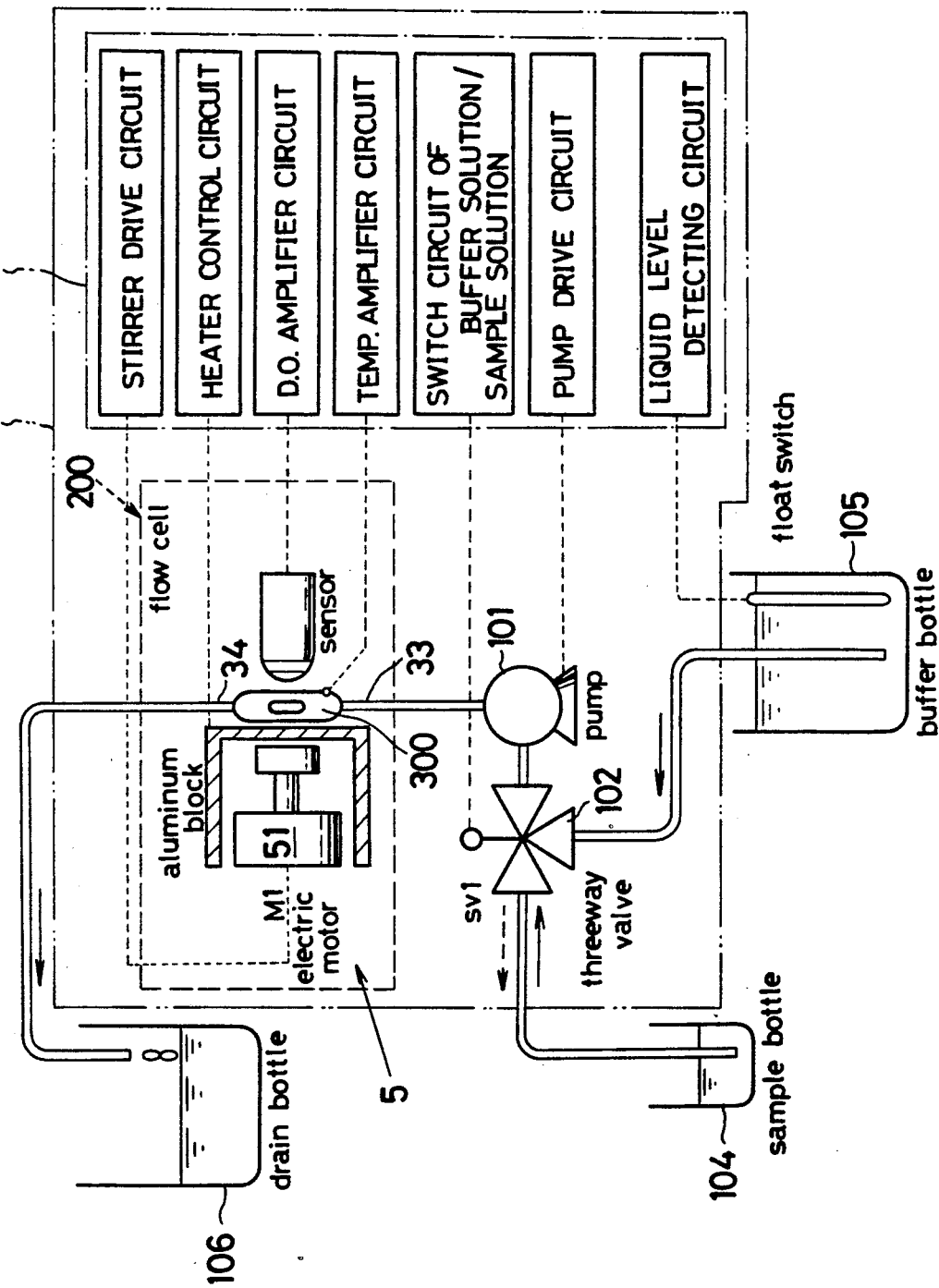

SULFUR DIOXIDE DETECTOR DEVICE EMBODIED BY USING S02-OXIDANT BIOAGENT

BACKGROUND OF THE INVENTION

1. Field of the Invention

The invention relates to a sulfur dioxide detector device using $SO_2$-oxidant bioagent in order to detect concentration of sulfurous acid contained in processed foods or the like.

2. Description of Prior

In order to detect concentration of sulfite used as an anti-oxidant in processed foods or the like, specified bioagent such as microbe and enzyme has been employed to oxidize sulfurous acid to sulfuric acid. An consumed amount of the dissolved oxygen is equivalent to the concentration of the sulfite in the anti-oxidant.

To embody the detection, a $SO_2$-detector device is introduced in which a bio-membrane is provided which has the bioagent between a gas permeable membrane and an immobilized membrane. Then, $SO_2$-involved solution is adapted circulate through an inlet, cell and outlet. When the $SO_2$-involved solution enters the cell, the solution flows along the gas permeable membrane to allow $SO_2$ to pass through the bio-membrane. During the passage of the $SO_2$, the $SO_2$ is oxidized to sulfuric acid by dissolved oxygen, an amount of which corresponds to an output difference occasioned from an oxygen concentration sensor.

In this $SO_2$-detector device, however, a fluctuation of liquid pressure and foam in the cell causes to deviate from an accurate concentration detection particularly when replenishing the $SO_2$-involved solution.

Further, the bio-membrane is attached to a spherical oxygen electrode of the oxygen concentration sensor, deliberate care and experienced skill are unavoidably needed when replacing the bio-membrane. It is also necessary to remove the bio-membrane whenever replacing a battery cell of the oxygen concentration sensor. This makes handling of the $SO_2$-detector device troublesome and complicated.

Therefore, it is an object of the invention to provide a sulfur dioxide detector device which is capable of quickly detecting sulfurous acid concentration with high accuracy.

It is another object of the invention to provide a sulfur dioxide detector device which is capable of replacing a battery cell and a bio-membrane individually, thus making handling of the device relatively easy.

SUMMARY OF THE INVENTION

According to the present invention, there is provided a sulfur dioxide detector device embodied by using $SO_2$-oxidant bioagent comprising: a horizontally arranged sensor housing; an oxygen concentration sensor removably disposed within sensor housing; a bio-membrane concentrically located at one end of the oxygen concentration sensor, the bio-membrane including the $SO_2$-oxidant bioagent provided between immobilized membrane and a gas permeable membrane; the oxygen concentration sensor having an oxygen electrode placed in contact with the immobilized membrane of the bio-membrane; a dish-shaped cell coaxially arranged with a horizontal line, and having an open end which is in contact with the gas permeable membrane of the bio-membrane so that $SO_2$-involved solution supplied to the dish-shaped cell causes to oxidize sulfurous acid during which the $SO_2$ permeates through the bio-membrane so as to generate an output from the oxygen concentration sensor depending on an amount of the $SO_2$; and an inlet and outlet hole each formed on a sidewall of the dish-shaped cell in diametrically opposed relationship, the outlet hole being always located right above the inlet hole so as to quickly drain foam occasioned at the time when the $SO_2$-involved solution is supplied to the dish-shaped cell through the inlet hole and drained from the outlet hole.

The outlet hole positions right above the inlet hole so that the foam inside the cell is smoothly drained from the outlet hole. Thus makes it possible to detect the $SO_2$ concentration with high accuracy.

Each opening of the inlet and outlet hole is directed slantwise to the gas permeable membrane, and making an angle with the axial direction of the dish-shaped cell within the range less than 90 degrees, preferably 20 to 30 degrees. The structure is such that the $SO_2$-involved solution comes to flow along the bio-membrane so as to restrain the foam from lingering on the bio-membrane.

Further, an opening area of the outlet hole is greater than that of the inlet hole. Preferably, the former is 2~4 times as great as the latter. This enables to readily drain the foam inside the cell from the outlet hole, and at the same time, avoiding the liquid pressure inside the cell from fluctuating when replenishing the $SO_2$-involved solution. Thus enables to keep a tightness between the bio-membrane and the oxygen electrode to accurately detect the $SO_2$ concentration.

Moreover, the dish-shaped cell has a relatively small volume capacity within the range from 0.3 ml to 0.6 ml. This leads to making the $SO_2$-involved solution contact with the bio-membrane quickly to accurately detect the $SO_2$ concentration for a very short period of time.

According further to the invention, a sulfur dioxide detector device embodied by using $SO_2$-oxidant bioagent further comprises a retainer frame removably disposed within the sensor housing in a manner to surround one end of the oxygen concentration sensor, a press ring removably fit around the retainer frame so as to retain a periphery of the bio-membrane between the retainer frame and the press ring.

The bio-membrane is retained by the retainer frame and the press ring so that the bio-membrane and the oxygen concentration sensor are individually replaced so as to make its handling easy.

The bio-membrane is removed by merely separating the retainer frame and the press ring when it is needed to replace the bio-membrane and the $SO_2$-oxidant bioagent. A newly replaced bio-membrane is placed on the open surface of the retainer frame. Then, the retainer frame is fit into the press ring to stretch the bio-membrane with uniform tension. Unevenly stretched bio-membrane deteriorates the tightness between the bio-membrane and the oxygen electrode, thus adversely affecting on the concentration detecting accuracy of the $SO_2$-involved solution.

Further, a support plate 31 is fixedly provided between the gas permeable membrane of the bio-membrane and the open end of the dish-shaped cell. The support plate has a central open window into which an O-ring is fit to elastically urge the bio-membrane against the oxygen electrode of the oxygen concentration sensor to more enhance the tightness between the bio-membrane and the oxygen electrode.

Various other objects and advantages to be obtained by the present invention will appear in the following description and in the accompanying drawings.

BRIEF DESCRIPTION OF THE DRAWINGS

FIG. 3 is schematic connecting diagram of a sulfur dioxide detector device embodied by using $SO_2$-oxidant bioagent.

DESCRIPTION OF THE PREFERRED EMBODIMENTS

Figure 1:
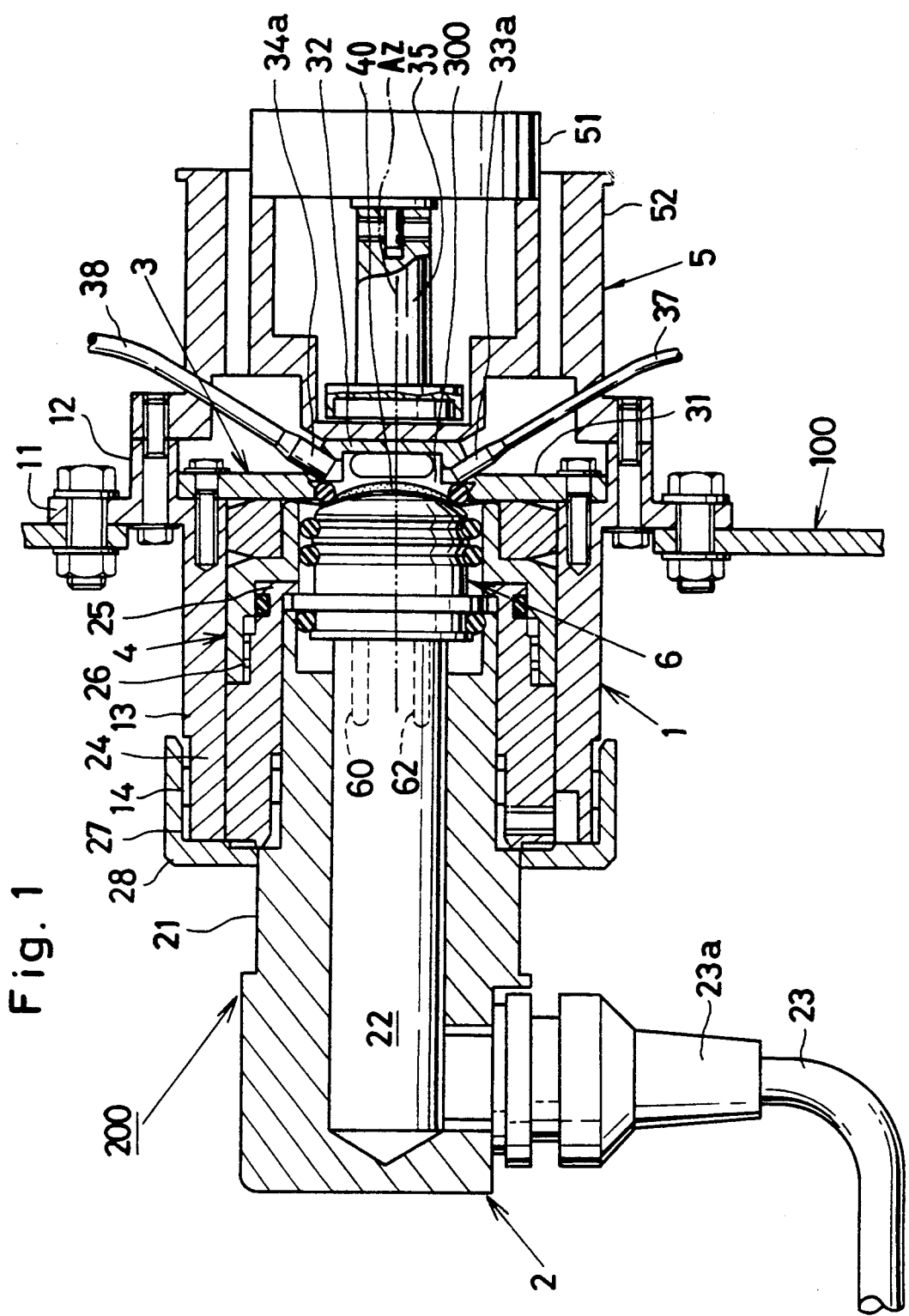
FIG. 1 is a longitudinal cross sectional view of a sulfur dioxide detector device embodied by using $SO_2$-oxidant bioagent according to the invention.
Figure 2:
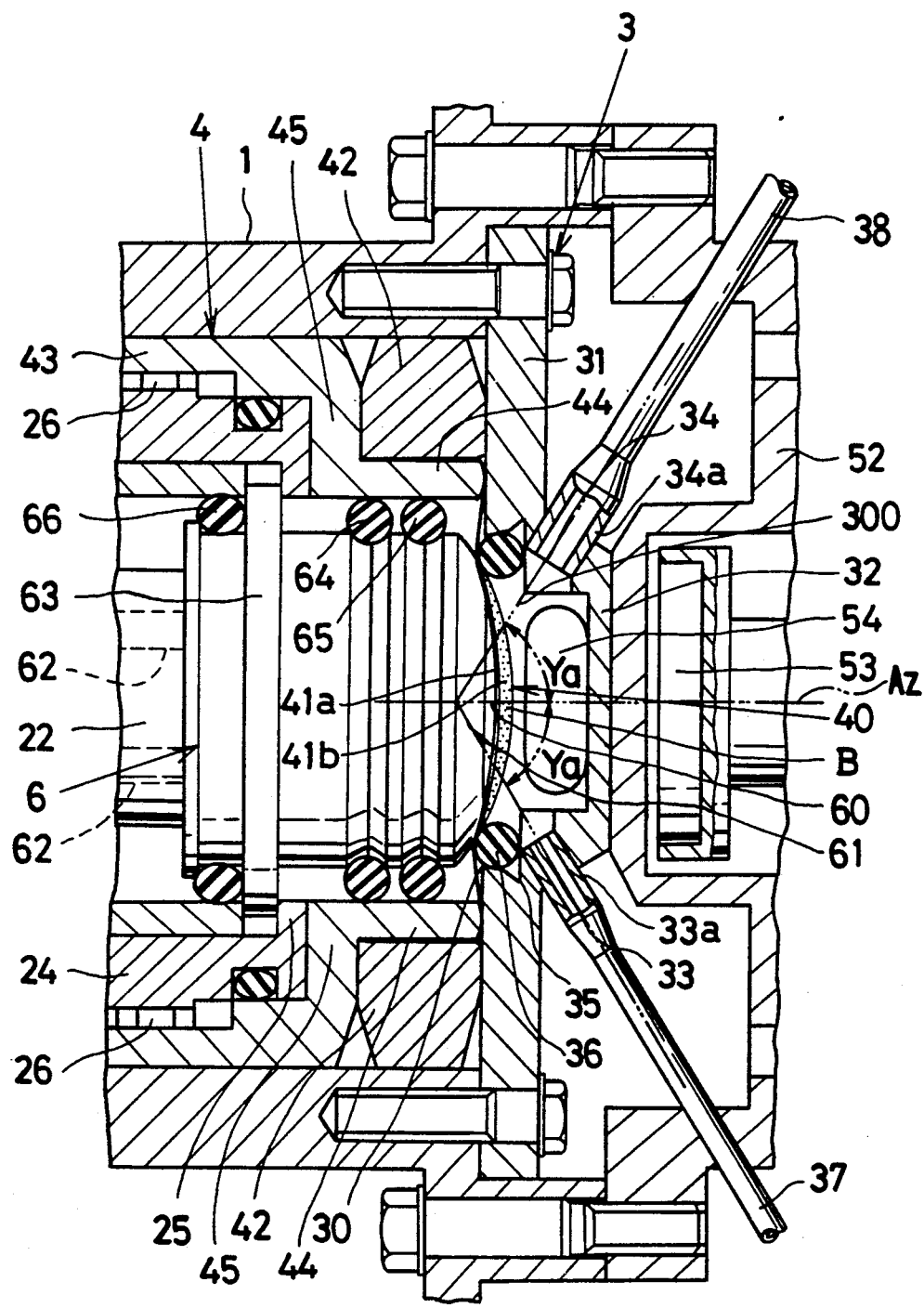
FIG. 2 is an enlarged main part of FIG. 1.

Referring to FIGS. 1 and 2, a sulfur dioxide detector device has a casing 100 in which a sensor 200 is horizontally disposed. The sensor 200 has a cylindrical housing 1 and an oxygen concentration sensor 2 removably disposed in the housing. A dish-shaped or frustoconical cell 32 is arranged to orient its axis Az in a horizontal direction. An inner space of the cell 32 serves as a detecting chamber 300, and an open end of the cell 32 is located to face to one end of the oxygen concentration sensor 2 to horizontally align with each other. Between the cell 32 and the oxygen concentration sensor 2, the support plate 31 is vertically located which has a central open window 30 which communicates with the open end of the cell 32. The support plate 31 acts to help support a bio-membrane 40 which carries $SO_2$-oxidant bioagent, and act as a chamber-forming structure 3 in cooperation with the cell 32 as described in detail hereinafter. The housing 1 has a detection housing 12 which encloses the cell 1, and a sensor housing 13 which encloses the oxygen concentration sensor 2. The detection housing 12 has an outer flange 11 in which the housing 12 meets the sensor housing 13. Within the detection housing 12, a pulsator device 5 is enclosed which has a stirrer 54 adapted to stir $SO_2$-involved solution within the cell 32 as described hereinafter. The oxygen concentration sensor 2 has a column-shaped oxygen concentration cell (electrochemical cell) 6 replaceably disposed in an outer shell of the sensor 2. One end of the oxygen concentration cell 6 carries a semi-spherical surface 61 whose central portion serves as an oxygen electrode 60 which meets the open end of the cell 32 through the open wondow 30 of the support plate 31. The oxygen concentration cell 6 further has an electrode terminal 62 extended to the other end portion remote from the semi-spherical surface 61. Around the oxygen concentration cell 6, an outer flange 63 is circumferentially placed, and at the same time, O-rings 64, 65 and 66 are encircled. The outer shell of the oxygen concentration sensor 2 is enclosed by a cylindrical handle 21, one open end of which is diametrically increased to partically receive the oxygen concentration cell 6, while the other end of the handle 21 extends beyond a left end of the sensor housing 13. Within the handle 21, a receptacle 22 to which the electrode terminal 62 is connected. At a left side of the handle 21, the handle 21 has an outlet 23a carrying a power source wire 23. Between the handle 21 and the sensor housing 13, an annular cell cap 24 is removable placed by means of a thread 26 provided with an diameter-decreased portion of the cap 24. A right open end of the cap 24 has an inner ring portion 25 which interposes the flange 63 in cooperation with a left open end of the handle 21. A housing cap 28 has a central opening which accepts the extended portion of the handle 21. The housing cap 28 has a female thread 27 which is removably screwed to a male thread 14 formed on an outer surface of the sensor housing 13 so as to serve as a stopper against a left end of the cell cap 24.

In the meanwhile, a retainer frame 4 has a diameter-reduced ring portion 44 which air-tightly encircles the oxygen concentration cell 6 by way of the O-rings 64, 65. The diameter-reduced ring portion 44 continuously extends through an intermediate wall 45 to integrally have a diameter-increased ring portion 43 having a female thread (not shown) which is screwed to the thread 26. A press ring 42 is removably disposed in the sensor housing 13 together with the retainer frame 4, and tightly encircled an outer surface of the diameter-reduced ring portion 44. Between the press ring 42 and the diameter-reduced ring portion 44, a circumferential periphery of the bio-membrane 40 is placed to retain the bio-membrane 40, the Upon mounting the bio-membrane 40, the bio-membrane 40 is put on an open end of the diameter-reduced ring portion 44 to adhere the periphery of the bio-membrane 40 to an outer surface of the diameter-reduced ring portion 44. Then, the press ring 42 is brought to tightly encircle around the diameter-reduced ring portion 44 through the periphery of the bio-membrane 40. This enables to stretch the bio-membrane 40 with uniform tension in a manner to be coaxially arranged with the oxygen concentration sensor 2 including the oxygen concentration cell 6. The bio-membrane 40, thus stretched, is brought at its central portion into tight engagement with the oxygen electrode 60 which somewhat protracts from the right open end of the diameter-reduced ring portion 44.

The bio-membrane 40 is a lamination of a gas permeable membrane 41b and a bag-shaped immobilized membrane 41a, an inside of which $SO_2$-oxidant bioagent (B) is immobilized. The $SO_2$-oxidant bioagent (B) is microbe selected from *Thiobacillus thiooxidans* and *Thiobacillus ferrooxidans*. Otherwise, the $SO_2$-oxidant bioagent (B) may be enzyme obtained from *Thiobacillus thiooxidans* or *Thiobacillus ferrooxidans*.

The support plate 31 located between the bio-membrane 40 and the cell 32, has an O-ring 36 fit into a groove 35 provided by bevelling an inner wall of the open window 30. The O-ring 36 somewhat protracts from the window 30 to elastically engage with the gas permeable membrane 41b so as to tightly urge the immobilized membrane 41a against the oxygen electrode 60.

At a sidewall of the frusto-cone or dish-shaped cell 32, there are provided an outlet hole 34 and inlet hole 33, which are diametrically opposed each other. The outlet hole 34 is located right above the inlet hole 33. Both the outlet hole 34 and inlet hole 33 are slanted with respect to the bio-membrane 40 to make an angle of 20~30 degrees with axial direction as the cell 32 as shown in FIG. 2. It is, however, noted that the angle made with the horizontal direction may be within the range of acute angle. An open area of the outlet hole 34 is designed to be 2~4 times as great as that of the inlet hole 33. To the outlet hole 34 and inlet hole 33, an outlet pipe 34a and inlet pipe 33a are in turn connected, each inner diameter of which corresponds to the outlet hole 34 and the inlet hole 33. To the outlet pipe 34a and the inlet pipe 33a, circulatory pipes 38, 37 are connected in turn so as to circulate $SO_2$-involved solution through the cell 32.

The pulsator device 5 has a cylindrical case 52 enclosed by the detection housing 12. In the case 52, an electric motor 51 is located which has a rotary shaft 53 extending to the detecting chamber 300 to drive the stirrer 54 within the cell 32 when the motor 51 is energized.

Within the casing 100, a pump 101 a three-way valve 102 and various kinds of control units including a control circuit 103 are disposed as shown in FIG. 3. By way of the three-way valve 102, the $SO_2$-involved solution from a sample bottle 104 or solution from a buffer bottle 105 is selectively supplied to the detection chamber 300 of the cell 32, and drained to a drain bottle 106 from the outlet hole 34.

When the $SO_2$-involved solution is transferred to the cell 32, and kept at an appropriate temperature, the $SO_2$-involved solution comes contact with the gas permeable membrane 41b. Then, $SO_2$ gas extricated from the $SO_2$-involved solution passes throught the gas permeable membrane 41b to encounter the microbe (B) which oxidizes sulfurous acid to produce oxygen gas. Then, the concentration of the oxygen dissolved in the microbe (B) decreases from e.g. 6 ppm to e.g. 2 ppm within a certain period of time. This causes to decrease the oxygen which reaches to the oxygen electrode 60 so as to reduce an output generated from the oxygen concentration sensor 2. The reduction of the output makes it possible to calculate the concentration of the sulfurous acid.

As understood from the foregoing description, the opening area of the outlet hole 34 is 2~4 times as great as that of the inlet hole 33 so that foam inside the detection chamber 300 is readily drained from the outlet hole 34. This also avoids liquid pressure inside the detection chamber 300 from rising excessively. The pressure fluctuation deteriorates the tightness between the bio-membrane 40 and the oxygen electrode 60 so as to adversely affect on the concentration detection.

The inlet hole 33 is slanted with respect to the biomembrane 40 to make the angle ya of 20~30 degrees with the axial direction az of the cell 32. This enables to flow the $SO_2$-involved solution along the bio-membrane 40 to avoids the foam from lingering on the bio-membrane 40 so as to keep good detection accuracy. In this instance, the cell 32 may be located to tilt against the bio-membrane 40 to obtain the same advantage as mentioned above.

The volume capacity (0.3 ml~0.6 ml) of the cell 32 is comparably small with relatively increased open end area of the cell 32. This leads to making the $SO_2$-involved solution contact with the bio-membrane quickly to accurately detect $SO_2$ concentration for a very short period of time.

The pump 101 makes it possible to purge the detection chamber 300 of the cell 32 by means of the buffer solution so as to avoid remnant of the $SO_2$-involved solution in the cell 32 to accurately detect $SO_2$ concentration.

The purging can be easily made by driving the stirrer 54 while supplying the buffer solution to the cell 32.

The outlet hole 34 positions right above the inlet hole 33 so that the foam inside the cell 32 is smoothly drained from the outlet hole 34. Thus makes it possible to detect $SO_2$ concentration with high accuracy.

The opening area of the outlet hole 34 is greater than that of the inlet hole 33 so that foam inside the detection chamber 300 is readily drained from the outlet hole 34, and at the same time, avoiding liquid pressure inside the detection chamber 300 from rising excessively due to an outlet pressure of the pump 101.

Upon replacing the microbe (B) and the battery cell 6, the oxygen concentration sensor 2 together with the retainer frame 4 is taken out by removing the housing cap 28 from the sensor housing 13. The replacement of the bio-membrane 40 and the microbe (B) is carried out by separating the press ring 42 from the retainer frame 4. A newly replaced bio-membrane is put on the open surface of the retainer frame 4. Then, the retainer frame 4 and the press ring 42 are fit each other to stretch the bio-membrane with uniform tension. Unevenly stretched bio-membrane deteriorates the tightness between the bio-membrane and the oxygen electrode 60, thus adversely affecting on the concentration detecting accuracy of the $SO_2$-involved solution.

By taking out the retainer frame 4 and the cell cap 24, the replacement of the oxygen concentration cell 6 is readily carried out without taking out the bio-membrane 40. Then, the oxygen concentration cell 6 is pulled from the receptacle 22. Thus, the replacement of the oxygen concentration cell 6 is carried out independently of the bio-membrane 40, and thus making the handling of the device relatively easy.

While the invention has been described with reference to the specific embodiments, it is understood that this description is not to be construed in a limiting sense in as much as various modifications and additions to the specific embodiments may be made by skilled artisan without departing from the spirit and scope of the invention.

What is claimed is:

1. A sulfur dioxide detector device using $SO_2$-oxidant bioagent, the detector device comprising:
    a horizontally arranged sensor housing;
    an oxygen concentration sensor removably disposed within the sensor housing;
    a bio-membrane concentrically located at one end of the oxygen concentration sensor, the bio-membrane including an $SO_2$-oxidant bioagent provided between an immobilized membrane and a gas permeable membrane;
    the oxygen concentration sensor having an oxygen electrode placed in contact with the immobilized membrane of the bio-membrane;
    a dish-shaped cell formed with a horizontally extending axis, and having an open end which is in contact with the gas permeable membrane of the bio-membrane so that $SO_2$-laden solution supplied to the cell oxidizes sulfurous acid into sulfuric acid as $SO_2$ permeates through the bio-membrane so as to change an output from the oxygen concentration sensor depending on an amount of $SO_2$; and
    an inlet hole and an outlet hole each formed on a sidewall of the cell in diametrically opposed relationship, the outlet hole being always located directly above the inlet hole so as to quickly drain foam formed when the $SO_2$-laden solution is supplied to the dish-shaped cell through the inlet hole and drained from the outlet hole, the inlet and outlet holes being directed toward the gas permeable membrane to make an angle with the axial direction of the cell of less than 90 degrees.

2. A sulfur dioxide detector device as recited in claim 1, wherein the bioactive agent is selected from the group consisting of Thiobacillus thiooxidans and enzyme derived from Thiobacillus ferroxidans.

3. A sulfur dioxide detector device as recited in claim 1, wherein an opening area of the outlet is 2~4 times as great as that of the inlet hole.

4. A sulfur dioxide detector device as recited in claim 1, wherein the dish-shaped cell has a volume capacity within the range from 0.3 ml to 0.6 ml.

5. A sulfur dioxide detector device as recited in claim 1, further comprising a retainer frame removably disposed within the sensor housing in a manner to surround one end of the oxygen concentration sensor, and a press ring removably fitted around the retainer frame so as to retain a periphery of the bio-membrane between the retainer frame and the press ring.

6. A sulfur dioxide detector device as recited in claim 5, wherein the oxygen concentration sensor is enclosed in a cylindrical handle which is removably disposed in the sensor housing.

7. A sulfur dioxide detector device as recited in claim 5, wherein a support plate is fixedly provided between the gas permeable membrane of the bio-membrane and the open end of the cell, the support plate having a central open window into which an O-ring is fitted to elastically urge the bio-membrane against the oxygen electrode of the oxygen concentration sensor.

* * * * *